(12) United States Patent
Dorrer et al.

(10) Patent No.: US 8,956,530 B2
(45) Date of Patent: Feb. 17, 2015

(54) SYSTEM FOR SEPARATING BODILY FLUID CONSTITUENTS AND METHOD FOR PRODUCING SUCH A SYSTEM

(75) Inventors: Christian Dorrer, Stuttgart (DE); Thomas Brettschneider, Kornwestheim (DE)

(73) Assignee: Robert Bosch GmbH, Stuttgart (DE)

( * ) Notice: Subject to any disclaimer, the term of this patent is extended or adjusted under 35 U.S.C. 154(b) by 67 days.

(21) Appl. No.: 13/542,831

(22) Filed: Jul. 6, 2012

(65) Prior Publication Data

US 2013/0175213 A1 Jul. 11, 2013

(30) Foreign Application Priority Data

Jul. 11, 2011 (DE) .......................... 10 2011 078 961

(51) Int. Cl.
*B01D 21/24* (2006.01)
*B01D 63/00* (2006.01)
(Continued)

(52) U.S. Cl.
CPC .............. *B01D 35/30* (2013.01); *A61M 5/165* (2013.01); *B01L 3/502707* (2013.01); *B01L 3/502753* (2013.01); *B01D 63/088* (2013.01); *B01D 67/0032* (2013.01); *B01D 69/12* (2013.01); *B01D 71/26* (2013.01); *B29C 65/1635* (2013.01); *B29C 65/5057* (2013.01); *B29C 66/5416* (2013.01); *G01N 33/491* (2013.01);
(Continued)

(58) Field of Classification Search
None
See application file for complete search history.

(56) References Cited

U.S. PATENT DOCUMENTS 3,568,746 A * 3/1971 Faroni et al. .................. 411/302
3,747,769 A * 7/1973 Brumfield ..................... 210/350
(Continued)

FOREIGN PATENT DOCUMENTS

DE 100 46 173 A1 3/2002
DE 10 2009 006 065 A1 7/2010
(Continued)

OTHER PUBLICATIONS

Vandelinder et al., Separation of Plasma from Whole Human Blood in a Continuous Cross-Flow in a Molded Microfluidic Device, Analytical Chemistry, Jun. 1, 2006, pp. 3765-3771, vol. 78, No. 11.
(Continued)

*Primary Examiner* — Nam Nguyen
*Assistant Examiner* — Richard Gurtowski
(74) *Attorney, Agent, or Firm* — Maginot, Moore & Beck LLP

(57) ABSTRACT

A system for separating bodily fluid constituents is disclosed. The system includes a first substrate which, in a first main surface, has a first cavity for holding a bodily fluid sample, a second substrate, which, in a first main surface facing the first substrate, has a second cavity) for holding constituents separated from the bodily fluid sample, which second cavity lies opposite to the first cavity, a filter layer, which is arranged between the first substrate and the second substrate and which is designed to separate constituents of the bodily fluid sample in the first cavity and to pass the separated constituents to the second cavity, and a first thermoplastic connection layer, which is arranged between the first substrate and the filter layer, interconnects the first main surface of the first substrate and the filter layer in a fluid-tight manner and has a cutout lying opposite to the first cavity.

13 Claims, 5 Drawing Sheets

(51) Int. Cl.

| | | |
|---|---|---|
| *B01D 27/08* | (2006.01) | |
| *B01D 35/30* | (2006.01) | |
| *A61M 5/165* | (2006.01) | |
| *B01L 3/00* | (2006.01) | |
| *B01D 63/08* | (2006.01) | |
| *B01D 67/00* | (2006.01) | |
| *B01D 69/12* | (2006.01) | |
| *B01D 71/26* | (2006.01) | |
| *B29C 65/16* | (2006.01) | |
| *B29C 65/50* | (2006.01) | |
| *B29C 65/00* | (2006.01) | |
| *G01N 33/49* | (2006.01) | |
| *B29C 65/48* | (2006.01) | |
| *B01D 21/30* | (2006.01) | |
| *B01D 69/10* | (2006.01) | |
| *B29L 31/14* | (2006.01) | |

(52) U.S. Cl.
CPC .......... *B29C 65/168* (2013.01); *B29C 65/4815* (2013.01); *B01D 21/30* (2013.01); *B01D 69/10* (2013.01); *B01D 2313/90* (2013.01); *B01D 2325/028* (2013.01); *B01L 2200/0689* (2013.01); *B01L 2300/0681* (2013.01); *B01L 2300/0887* (2013.01); *B29C 65/1612* (2013.01); *B29L 2031/14* (2013.01); *B29C 66/30325* (2013.01); *B29C 66/71* (2013.01); *B29C 66/73366* (2013.01); *B29C 66/7352* (2013.01); *B29C 66/73921* (2013.01); *B29C 65/1645* (2013.01)
USPC ..... 210/109; 210/97; 210/321.6; 210/321.72; 210/350; 210/484; 210/645

(56) References Cited

U.S. PATENT DOCUMENTS

| | | | | |
|---|---|---|---|---|
| 4,919,996 | A | * | 4/1990 | Dewar et al. ................... 428/221 |
| 5,688,258 | A | * | 11/1997 | Rawat et al. .............. 604/385.13 |
| 6,437,551 | B1 | * | 8/2002 | Krulevitch et al. .......... 324/71.1 |
| 2003/0213551 | A1 | * | 11/2003 | Derand et al. .............. 156/272.2 |
| 2008/0128341 | A1 | | 6/2008 | Jang et al. |
| 2009/0120865 | A1 | | 5/2009 | Chung et al. |

FOREIGN PATENT DOCUMENTS

| | | |
|---|---|---|
| DE | 10 2009 024 495 A1 | 12/2010 |
| DE | 10 2010 025 516 A1 | 12/2011 |

OTHER PUBLICATIONS

Ehrfeld, W. et al., Fabrication of Components and Systems for Chemical and Biological Microreactors, Conference on Microreaction Technology IMRET, 1997, 72-89, Springer Verlag, Berlin, Germany.

* cited by examiner

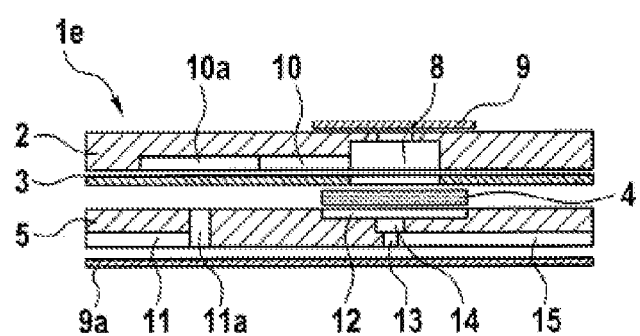
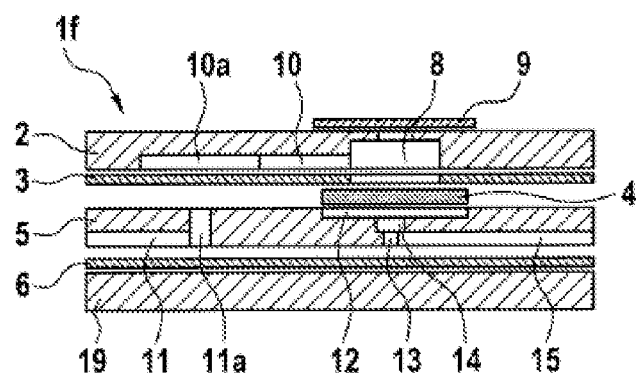
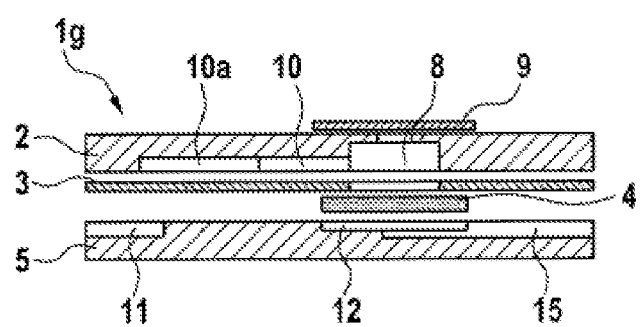

SYSTEM FOR SEPARATING BODILY FLUID CONSTITUENTS AND METHOD FOR PRODUCING SUCH A SYSTEM

This application claims priority under 35 U.S.C. §119 to patent application no. DE 10 2011 078 961.8, filed on Jul. 11, 2011 in Germany, the disclosure of which is incorporated herein by reference in its entirety.

The disclosure relates to a system for separating bodily fluid constituents, more particularly for separating blood plasma from whole blood, and to a method for producing such a system.

BACKGROUND

In medical technology, particularly in diagnostics, bodily fluid samples are often preconditioned so that it is possible to perform a diagnosis on the basis of the constituents of the samples. The constituents of the bodily fluid samples must often be separated for this purpose, with filters often being used for this.

An example relates to separating blood plasma from whole blood. Blood cells can be filtered out of a blood stream with the aid of a filter membrane while the blood plasma can pass the filter membrane. Lab-on-chip (LOC) systems offer the advantage of ensuring an automated progress of diagnostic assays such that operating errors can be minimized. Such systems moreover lower the costs of the analysis procedure because smaller sample volumes can be analyzed in a very short time.

By way of example, an LOC system is proposed in the article VanDelinder, V., Groisman, A., Anal. Chem. 2006, 78, 3765, in which blood plasma can be separated out of whole blood with the aid of cross-flow filtration through a microstructured sieve.

The document US 2008/0128341 A1 teaches a micro-filtration system, in which whole blood is pumped through a microstructure in a microchannel, and so merely the blood plasma can pass the microstructure.

The document US 2009/0120865 A1 discloses a multi-layered substrate with an embedded filter unit, in which the blood plasma can be separated from whole blood.

SUMMARY

According to one embodiment, the present disclosure relates to a system for separating bodily fluid constituents, with a first substrate which, in a first main surface, has a first cavity for holding a bodily fluid sample, a second substrate, which, in a first main surface facing the first substrate, has a second cavity for holding constituents separated from the bodily fluid sample, which second cavity lies opposite to the first cavity, a filter layer, which is arranged between the first substrate and the second substrate and which is designed to separate constituents of the bodily fluid sample in the first cavity and to pass the separated constituents to the second cavity, and a thermoplastic connection layer, which is arranged between the first substrate and the filter layer, interconnects the first main surface of the first substrate and the filter layer in a fluid-tight manner and has a cutout lying opposite to the first cavity.

According to a further embodiment, the present disclosure relates to a method for producing a system for separating bodily fluid constituents, comprising the steps of arranging a thermoplastic connection layer on a first main surface of a first transparent substrate, which, in a first main surface, has a first cavity for holding a bodily fluid sample, of arranging a filter layer on the thermoplastic connection layer, of irradiating the thermoplastic connection layer through the first transparent substrate by means of a laser beam such that the thermoplastic connection layer fuses with the first substrate and the filter layer in the region of the laser beam, forming a fluid-tight connection seam, and of arranging on the filter layer a second transparent substrate, which, in a first main surface facing the first substrate, has a second cavity, which lies opposite to the first cavity, for holding constituents separated from the bodily fluid sample.

With a system for separating bodily fluid constituents according to the disclosure, it becomes possible to attach a filter layer between two substrates in a mechanically stable and fluid-tight manner. This is achieved by virtue of the fact that a thermoplastic connection layer is provided between the substrates or between the first substrate and the filter layer. As a result of laser welding, the first substrate can be connected to the thermoplastic connection layer in a mechanically stable manner while forming a fluid-tight connection seam. In the process, there is simultaneous partial capillary penetration of the molten thermoplastic connection layer into the filter layer, as a result of which a stable and fluid-tight connection is also created between the filter layer and the thermoplastic connection layer. As a result of the fluid-tight property of the created connections between the substrates and between the substrates and the filter layer, fluid paths around the filter layer can be avoided. As a result, it can advantageously be ensured that there is complete and total filtering of the bodily fluid samples.

Such systems and the production methods thereof first of all offer the advantage that the whole design can be joined in one single process step. This saves manufacturing costs and reduces the manufacturing time.

Secondly, it is possible to dispense with adhesives for connecting the substrates to the filter layer or for connecting the substrates to one another. This reduces the manufacturing complexity and completely avoids the problem of constituents of the adhesive undesirably being able to pass into the sample liquid.

The connection technique according to the disclosure can be used to implement almost any dimensions for cavities, filter layers and microchannels. Here, each of the systems can be designed such that separation of constituents in bodily fluid samples is made possible in a single filtering step.

The first cavity can advantageously extend from the first main surface of the first substrate to a second main surface of the first substrate lying opposite the first main surface, wherein the system can furthermore comprise an adhesive film which is detachably arranged on the second main surface of the first substrate and covers the first cavity. The advantage offered by this is that the introduction of the bodily fluid sample into the cavity is made simpler without requiring special connection elements.

In a preferred embodiment, the first cavity can extend from the first main surface of the first substrate to a second main surface of the first substrate lying opposite the first main surface, wherein the system furthermore comprises a third substrate, which is arranged on the second main surface of the first substrate and covers the first cavity, and a further thermoplastic connection layer, which is arranged between the third substrate and the first substrate and interconnects the third substrate and the first substrate in a fluid-tight manner. This design renders it possible in a quick and simple manner to route separated constituents of bodily fluid samples on for further analysis and diagnosis in the second substrate.

The second substrate can preferably have a cutout in the first main surface, in which cutout the filter layer is arranged, and the thermoplastic connection layer can interconnect the first main surface of the first substrate and the first main surface of the second substrate in a fluid-tight manner. This offers the advantage of also being able to use relatively thick filter layers, without the distance between the two substrates becoming too large. As a result, an optimal mechanical connection between the two substrates is possible via the thermoplastic connection layer.

The system according to the disclosure can comprise a first microchannel in the first substrate, which first microchannel is connected to the first cavity and which is designed to be actuated with gas pressure such that the bodily fluid sample situated in the first cavity is pressed out of the first cavity through the filter layer. The second substrate can preferably comprise a pressure channel on the first main surface, which pressure channel adjoins a main surface of the thermoplastic connection layer, wherein the first microchannel can adjoin the opposing main surface of the thermoplastic connection layer, and wherein the pressure channel can be designed to be actuated with gas pressure such that the thermoplastic connection layer penetrates into the first microchannel under elastic deformation and produces corresponding gas pressure in the first microchannel. As a result of this form of pneumatic operation there can advantageously be precise and automatic control of the separation process.

In the second substrate, the system according to the disclosure includes a second microchannel, which is connected to the second cavity, and a third microchannel, which is connected to the second cavity, wherein the second microchannel can be designed to be actuated with gas pressure such that the separated constituents of the bodily fluid sample situated in the second cavity are pressed out of the second cavity through the third microchannel. Furthermore, in a preferred embodiment, the system can comprise a microsensor, which is arranged in a sensor region in the first main surface of the first substrate, wherein the thermoplastic connection layer can have a cutout lying opposite to the sensor region, and wherein the third microchannel can run on the first main surface of the second substrate in the region of the cutout lying opposite to the sensor region such that separated constituents of the bodily fluid sample which are pressed through the third microchannel come into contact with the microsensor. It is possible to create an autonomous diagnosis system with the aid of integrating a microsensor provided for the analysis of the separated constituents of the bodily fluid sample, which diagnosis system enables a fully-automatic, quick and efficient analysis of bodily fluid samples.

Preferred developments are the subject matter of the respective dependent claims.

To the extent that this is meaningful, the embodiments and developments presented above can be combined together in any form. Further possible embodiments include combinations of features set that have not been explicitly mentioned, which features were described above or will be described below with respect to the exemplary embodiments.

BRIEF DESCRIPTION OF THE DRAWINGS

Further features and advantages of embodiments of the disclosure emerge from the following description with reference to the appended drawings.

In detail:

FIG. 6 shows a schematic illustration of a sectional view through the system for separating bodily fluid constituents from FIG. 5 as per a further embodiment of the disclosure;

FIG. 7 shows a schematic illustration of a system for separating bodily fluid constituents as per a further embodiment of the disclosure;

FIG. 8 shows a schematic illustration of a system for separating bodily fluid constituents as per a further embodiment of the disclosure;

Figure 1:
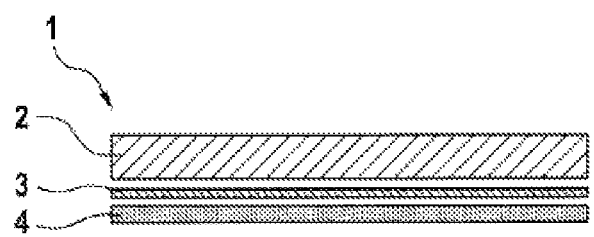
FIG. 1 shows a schematic illustration of polymer layers as a basis for a separation system as per one embodiment of the disclosure.

In the figures of the drawing, equivalent and functionally equivalent elements, features and components are—to the extent that nothing else is said—respectively provided with the same reference signs. It is understood that components and elements are not necessarily reproduced true to scale in the drawings for reasons of clarity and intelligibility.

DETAILED DESCRIPTION

Within the meaning of the present disclosure, bodily fluid samples can be any aqueous solutions or suspensions that are taken from human or animal bodies. By way of example, bodily fluids may comprise blood, urine, saliva, lymph, bile, gastric juices, sweat, pus, sperm or any other secretions of the human or animal body. Constituents of bodily fluids are particles, e.g. cells or bacteria, which can be separated from the rest of the bodily fluid by filtration, and dissolved substances. In the following text, reference is made in particular to whole blood, which has e.g. blood cells and blood plasma as separable constituents.

FIG. 1 shows a schematic illustration of polymer layers as a basis for a separation system 1. A first thermoplastic connection layer 3 is arranged on a main surface of a first substrate 2. Here, the first substrate 2 can have a small thickness compared to the width and depth of the first substrate 2 such that the substantially planar surface defined by the width and depth of the first substrate 2 forms a first main surface of the first substrate 2. Correspondingly, a second main surface of the first substrate 2 can denote a surface which is situated parallel to the first main surface and is offset with respect to the first main surface by the thickness of the first substrate 2. A filter layer 4 is in turn arranged on the first thermoplastic connection layer 3. By way of example, the first substrate 2 can comprise a thermoplastic, for example polycarbonate, polypropylene, polyethylene, polymethyl methacrylate, cyclic olefin copolymer or other thermoplastic substances. The first substrate 2 can have a thickness of between 0.5 mm and 3 mm, more particular approximately 1 mm, and be transparent. The first thermoplastic connection layer 3 can for example comprise a thermoplastic elastomer and have a thickness of between 20 μm and 500 μm, more particularly approximately 50 μm. By way of example, the filter layer 4 can comprise a fabric filter, a silica filter, a plasma separation membrane or any other filter membranes which are suitable for separating corresponding constituents of bodily fluids, for example blood plasma from whole blood. The filter layer 4 can comprise a thickness of between 50 μm and 2 mm.

The first substrate 2, the first thermoplastic connection layer 3 and the filter layer 4 can be pressed onto one another to form a mechanically stable connection. Then the first thermoplastic connection layer 3 can be irradiated by a laser beam through the first substrate 2. By way of example, a laser with a wavelength in the infrared range can be used for this purpose. At those points where the laser beam is incident on the first thermoplastic connection layer 3, the first thermoplastic connection layer 3 and the first substrate 2 fuse such that this results in a fusion bond between the two materials in the region of the laser beam. It is therefore possible to form a connection seam between the first thermoplastic connection layer 3 and the first substrate 2 by targeted guiding of the laser beam over the surface of the first thermoplastic connection layer 3.

Moreover, the fused first thermoplastic connection layer 3 can be pulled into the filter layer 4 by capillary forces, as a result of which there is a connection between the first thermoplastic connection layer 3 and the filter layer 4 in the region of the laser beam. The connections created thus between first substrate 2, first connection layer 3 and filter layer 4 are mechanically stable and fluid-tight.

Figure 2:
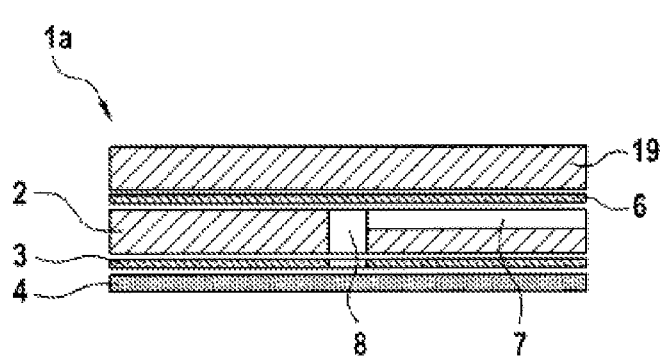
FIG. 2 shows a schematic illustration of polymer layers as a basis for a separation system as per a further embodiment of the disclosure.

FIG. 2 shows a schematic illustration of polymer layers as a basis for a separation system 1a. FIG. 2 differs from FIG. 1 in that a first cavity 8 is formed in the first substrate 2, which first cavity can extend through the first substrate 2. By way of example, the first cavity 8 can have a diameter of between approximately 1 and 30 mm, more particularly approximately 5 mm. Furthermore, a fourth microchannel 7 can be formed in the first substrate 2, the former having a fluid connection to the first cavity 8. The openings of the first cavity 8 and of the fourth microchannel 7 on the main surface of the first substrate 2 facing away from the filter layer 4 can for example be sealed to the outside by a third substrate 19, which is connected to the first substrate 2 by a second thermoplastic connection layer 6. Like the first thermoplastic connection layer 3, the second thermoplastic connection layer 6 can be connected to the first substrate 2 and the third substrate 19 by laser welding.

The first thermoplastic connection layer 3 moreover has a cutout which is formed in the region of the first cavity 8 and which enables bodily fluids, which may be situated within the first cavity 8, to pass into the filter layer 4.

Figure 3:
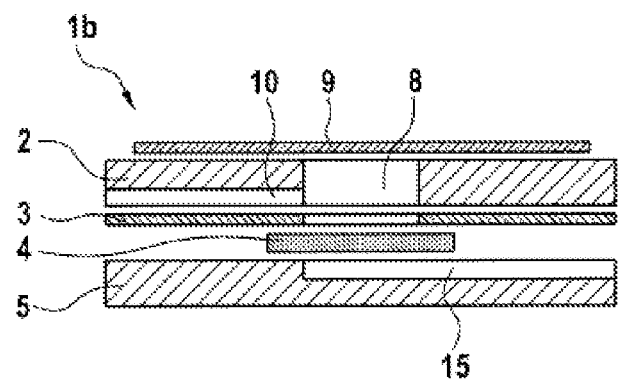
FIG. 3 shows a schematic illustration of polymer layers as a basis for a separation system as per a further embodiment of the disclosure.

FIG. 3 shows a further schematic illustration of polymer layers as a basis for a separation system 1b. FIG. 3 differs from FIG. 2 in that, instead of the third substrate 19 and the second thermoplastic connection layer 6, a first adhesive film 9 is arranged on the main surface of the first substrate 2 facing away from the filter layer 4. The first adhesive film 9 can be detachably connected to the first substrate 2 such that, when the first adhesive film 9 is removed from the first substrate 2, an access to the first cavity 8 is exposed, for example for filling a bodily fluid sample into the first cavity 8. After the first cavity 8 was filled, the first adhesive film 9 can be re-stuck onto the first substrate 2 such that the first cavity 8 is re-sealed with respect to the outside world. By way of example, the first adhesive film 9 can have a thickness of between 50 μm and 500 μm, more particularly approximately 100 μm. In an alternative embodiment, a bodily fluid sample can also be filled into the first cavity 8 through a fluidic plug-in or screwed connection, for example a Luer plug-in connection.

The first substrate 2 can moreover have a first microchannel 10, by means of which gas pressure can be applied to the first cavity 8. A bodily fluid sample in the first cavity 8 can be pressed through the filter layer 4 as a result of the gas pressure. The gas pressure can be produced in the first microchannel 10 in a controllable manner.

In FIG. 3, the filter layer 4 can be embodied with restricted lateral dimensions compared to the first substrate 2. By way of example, the filter layer 4 can be a disk with an area of between 25 mm$^2$ and 1000 mm$^2$, more particularly approximately 200 mm$^2$. Arranged on the lower side of the filter layer 4 there can be a second substrate 5, which, in the region below the filter layer 4, has a third cavity or a third microchannel 15, which can be reached by separated constituents, which pass through the filter layer 4, of a bodily fluid sample situated in the first cavity 8. A transverse fluid flow through the filter layer is advantageously possible using the design from FIG. 3.

Here, the second substrate 5 can have a similar design to the first substrate 2. Like in FIG. 1, the first thermoplastic connection layer 3 can be connected to the second substrate 5 by using a laser welding method. To this end, the first thermoplastic connection layer 3 can be irradiated through the second substrate 5 in regions outside of the area of the filter layer 4. A mechanically stable and fluid-tight connection is once again formed in the irradiation region between the first thermoplastic connection layer 3 and the second substrate 5 as a result of local fusion processes. Here, the first thermoplastic connection layer 3 is compressed in the region of the filter layer 4 and thus compensates for differences in height. To this end, it can be advantageous to select the thickness of the filter layer 4 to be so thin or to select the thickness of the first thermoplastic connection layer 3 to be so thick that too large a tension is not formed in the workpiece.

Figure 4:
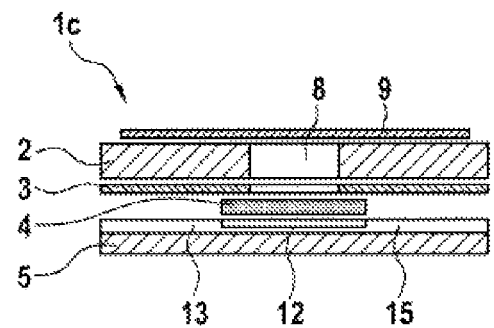
FIG. 4 shows a schematic illustration of polymer layers as a basis for a separation system as per a further embodiment of the disclosure.

FIG. 4 shows a schematic illustration of polymer layers as a basis for a separation system 1c. The design in FIG. 4 differs from the design shown in FIG. 3 in that provision is made in the second substrate 5 for a cutout on the main surface which faces the filter layer 4, in which cutout the filter disk 4 can at least partly be accommodated. As a result use can also be made of thicker filter disks 4 without the distance between the two first and second substrates 2 and 5 becoming too great or without too large a tension building up in the component.

By way of example, the third microchannel 15 in FIG. 4 can have hydrophilized walls such that, as a result of capillary forces, it is possible to fill the third microchannel 15 through the filter disk 4 with separated constituents of the bodily fluid sample in the first cavity 8. By way of example, the hydrophilization of the second substrate 5 or of the third microchannel 15 can be brought about by treatment with oxygen plasma. The advantage offered by this is that it is possible to dispense with covering the first cavity 8 by a first adhesive film 9. Furthermore, it is also possible to dispense with the airing channel or the first microchannel 10 from FIG. 3.

In one variation, a second microchannel 13 can be provided in FIG. 4 as a pressure channel in which pressure can be built up after filling the third microchannel 15 using capillary forces, and so the separated constituents in the third microchannel 15 can be rinsed out in a targeted manner. In order to control the aeration of the pressure channel 13 and to build up a targeted rinsing pressure, provision can for example be made for a microvalve in the pressure channel 13.

The channel cross sections of the first, second and third microchannels 10, 13 and 15, respectively, in FIGS. 3 and 4 can be between approximately 100×100 µm² and 1000×1000 µm², more particularly approximately 300×300 µm².

Figure 5:
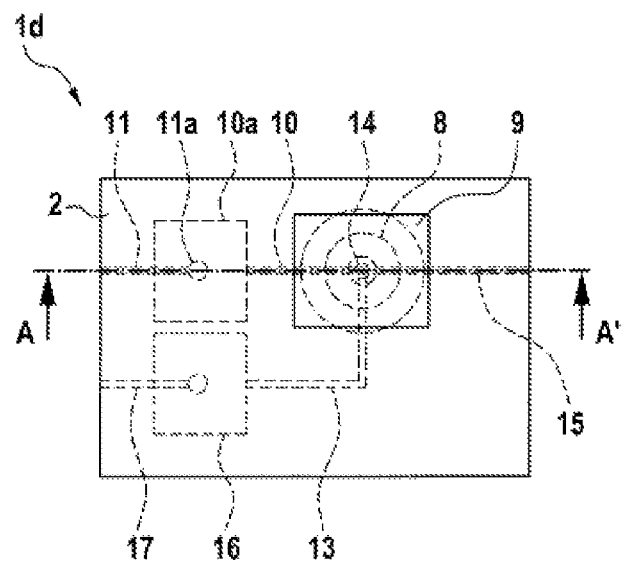
FIG. 5 shows a schematic illustration of a plan view of a system for separating bodily fluid constituents as per a further embodiment of the disclosure.

FIG. 5 shows a schematic illustration of a plan view of a system 1d for separating bodily fluid constituents. In FIG. 6, the system 1d from FIG. 5 is shown as system 1e in a sectional view along the section edge AA' illustrated in FIG. 5. As shown in FIG. 1 to FIG. 4, the system 1d or the system 1e has a first substrate 2 with a first cavity 8, over which a first adhesive film 9 is detachably arranged on a main surface, situated on top, of the first substrate 2. Moreover, the first cavity 8 is in fluidic connection with a first microchamber 10a via a first microchannel 10, with the first cavity 8, the first microchannel 10 and the first microchamber 10a having been introduced into the first substrate 2 by e.g. milling, injection molding, hot stamping or similar structuring techniques.

A first thermoplastic connection layer 3 has been applied to the lower main surface of the first substrate 2 in FIG. 6, said connection layer having a cutout level with the first cavity 8 such that the first cavity 8 has a fluidic connection to a filter layer 4 situated therebelow. In this case, the first microchannel 10 and the first microchamber 10a can be covered by the first thermoplastic connection layer 3 in a fluid-tight manner and held in a fluid-tight manner. Arranged on the first thermoplastic connection layer 3 there is a filter layer 4, which can for example assume the form of a filter disk and which can be arranged in a cutout 12 of a second substrate 5 lying therebelow. The cutout 12 can in this case have the shape of the filter disk 4.

A through-hole or a second cavity 14 is formed in the second substrate 5, which faces the first substrate 2 with a main surface, and has a fluid connection to the second and third microchannels 13 and 15 on the main surface of the second substrate 5 facing away from the first substrate 2. Here, the third microchannel 15 can be a rinsing channel, in which separated constituents of a bodily fluid sample situated in the first cavity 8 can collect. By contrast, the second microchannel 13 can be a pressure channel, which is connected to a second microchamber 16 in the substrate 5. The second and third microchannels 13 and 15, respectively, and also the second microchamber 16, the though-hole or the second cavity 14 and the cutout 12 can have been introduced into the second substrate 5 by e.g. milling, injection molding, hot stamping or similar structuring techniques.

A second adhesive film 9a, which seals the second and third microchannels 13 and 15 in the second substrate 5 in a fluid-tight manner, can be arranged on the main surface of the second substrate 5 facing away from the first substrate 2.

In the following text, the exemplary embodiments shown in FIGS. 5 and 6 will be used to explain an exemplary functionality of the system 1d or 1e for separating blood plasma out of a whole-blood sample.

The first adhesive film 9 is removed from the first substrate 2 and a whole-blood sample is pipetted into the first cavity 8. Subsequently, the first adhesive film 9 is connected to the first substrate 2 in order to seal the first cavity 8. An overpressure is applied to a first pneumatic pressure channel 11, which has been introduced into the second substrate 5, and this pressure is transmitted to the first thermoplastic connection layer 3 via a breakthrough 11a through the second substrate 5. In this case, the breakthrough 11a is situated opposite to the first microchamber 10a in the first substrate 2 such that the first thermoplastic connection layer 3 is elastically deflected into the first microchamber 10a as a result of the overpressure, i.e. the first thermoplastic connection layer 3 acts as pressure membrane for transmitting pressure from the first pressure channel 11 in the second substrate 5 into the first microchannel 10 in the first substrate 2. The overpressure in the first microchannel 10 is transferred to the first cavity 8, in which the whole blood is situated, which as a result of this is pressed through the cutout in the first thermoplastic connection layer 3 and through the filter disk 4.

The overpressure p acting in the first cavity 8 at the start of the filtering process can be estimated as follows:

$$p = p0 \cdot (V8 + V10 + V10a) \cdot (V8 + V10)^{-1},$$

where p0 is the ambient pressure and Vx respectively denotes the volumes of the hollow spaces in the first substrate 2 denoted by x. By way of example, the volume of the first microchannel 10 is denoted by V10. As a result of suitable dimensioning of volumes V8, V10 and V10a it is possible to set the overpressure p precisely in advance because p only depends on the defined volume ratio of the volumes V8, V10 and V10a and is therefore independent of the amount of pressure applied to the first pneumatic pressure channel 11. The overpressure p is reduced when the whole-blood sample is pressed through the filter layer 4. As a result of the filtering, only the blood plasma passes through the filter layer 4 and it is captured in the through-hole or the second cavity 14 and collected in the third microchannel 15.

Once the overpressure p has been reduced, the separation of the blood plasma is complete. In a next step it is possible for a further overpressure to be applied to a second pneumatic pressure channel 17 in the first substrate 2, which overpressure is transferred to the second microchamber 16 in the second substrate 5 via the first thermoplastic connection layer 3 by means of a mechanism similar to the one described with reference to the breakthrough 11a and the first microchamber 10a. The overpressure is transferred from the second microchamber 16 to the third microchannel 15 via the second microchannel 13 in the second substrate 5, and so the collected blood plasma is pushed out of the system 1d or the system 1e through the third microchannel 15. The obtained blood plasma is then available for further diagnostic processing. An advantage of the method is, inter alia, that, by setting the dimensions of the second microchamber 16 and the corresponding second and third microchannels 13 and 15, it is possible to set how much volume is displaced, i.e. how much blood plasma is pressed out of the system 1d or the system 1e. As a result, the blood plasma can for example be placed precisely level with a subsequent analysis and diagnostic apparatus. The path by which the blood plasma is moved is once again independent of the pressure applied to the second pneumatic pressure channel 17.

FIG. 7 shows a schematic illustration of a system 1f for separating bodily fluid constituents. The system 1f in FIG. 7 differs from the system 1e in FIG. 6 in that a second thermoplastic connection layer 6 and a third substrate 19 are arranged on the underside of the second substrate 5 instead of the second adhesive film 9a.

FIG. 8 shows a schematic illustration of a system 1g for separating bodily fluid constituents. The system 1g in FIG. 8 differs from the system 1e in FIG. 6 in that all microchannels and cutouts in the second substrate 5 do not extend up to the main surface of the second substrate 5 facing away from the first substrate 2 such that it is possible to dispense with a seal of the second substrate 5 on this main surface.

Figure 9:
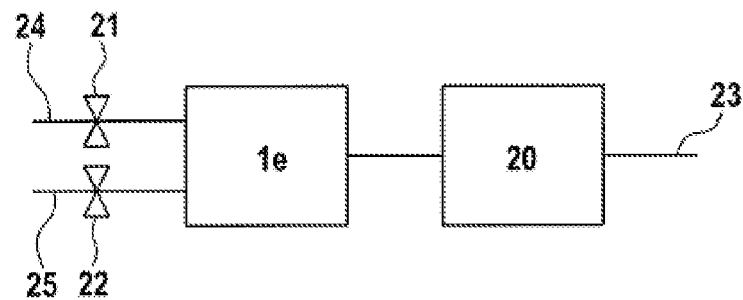
FIG. 9 shows a functional block diagram of a system for separating bodily fluid constituents as per a further embodiment of the disclosure.

FIG. 9 shows a functional block diagram of a system for separating bodily fluid constituents, more particularly for a system 1e, which is illustrated in FIG. 5. It is understood that one of the systems 1, 1a, 1b, 1c, 1d, 1f, 1g, 1h or 1j can also likewise be used in FIG. 9 instead of system 1e. The first and second pneumatic pressure channels 11 and 17 of system 1e are in this case connected to first and second lines 24 and 25, to which overpressure has been applied, via first and second pneumatic valves 21 and 22. The first and second valves 21 and 22 can be closed and opened in a controllable fashion and can either be embodied as external valves or be integrated into the first and second substrates 2 and 5 of the system 1e. The system 1e is connected to a detection apparatus 20, in which a sensor apparatus or measuring apparatus can be arranged, which is designed to detect biomolecules, e.g. proteins, cardiac markers, cancer markers or other substances in the blood plasma, which was separated from a whole-blood sample by the system 1e. Here, this can, for example, be an electronic, electrochemical, optical or other analysis system. If need be, further steps for preparing the sample, e.g. for carrying out an immune assay, can also be carried out in the detection apparatus 20. The detection apparatus 20 can be connected in fluidic fashion to ambient pressure by means of a ventilation connector 23.

Figure 10:
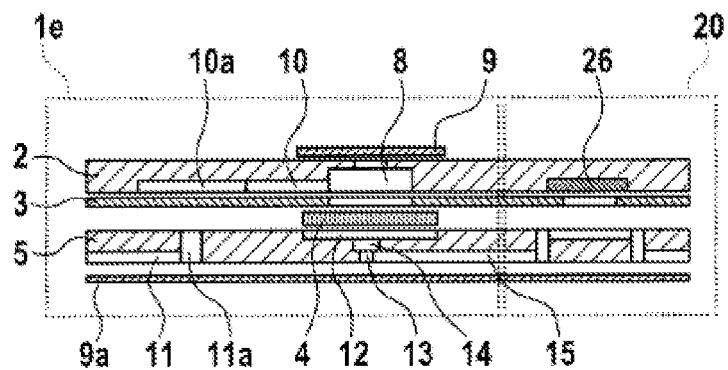
FIG. 10 shows a schematic illustration of a system for separating bodily fluid constituents as per a further embodiment of the disclosure.
Figure 11:
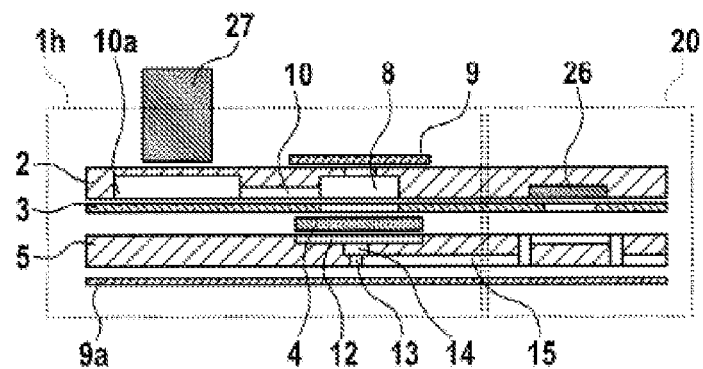
FIG. 11 shows a schematic illustration of a system for separating bodily fluid constituents as per a further embodiment of the disclosure.
Figure 12:
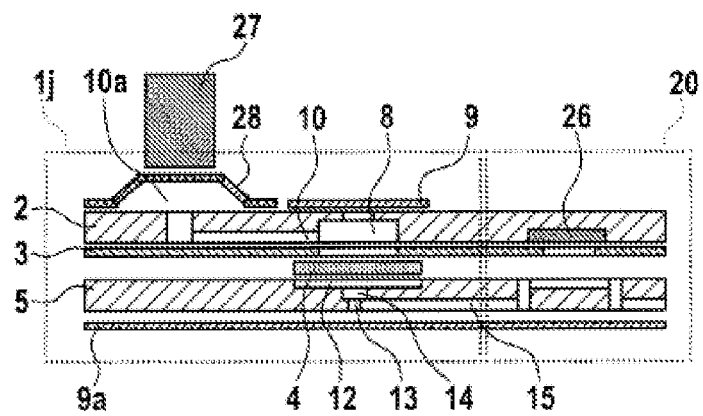
FIG. 12 shows a schematic illustration of a system for separating bodily fluid constituents as per a further embodiment of the disclosure.

FIGS. 10, 11 and 12 show exemplary embodiments for the system described in FIG. 9. The system shown in FIG. 10 differs from the systems shown in FIGS. 5 to 8 in that a microsensor 26 is furthermore arranged in the first substrate 2, the active surface of which microsensor is connected in fluidic fashion to the main surface of the second substrate 5 facing the first substrate 2 via a cutout in the first thermoplastic connection layer 3. The third microchannel 15 is guided in the second substrate 5 such that it runs on the main surface of the second substrate 5 facing the first substrate 2 in the region of the cutout formed opposite to the microsensor 26 in the first thermoplastic connection layer 3. When rinsing the blood plasma in the third microchannel 15, the overpressure can be set such that the blood plasma moves precisely so far that it reaches the region of the microsensor 26. The blood plasma then comes into contact with the active surface of the microsensor 26 and can be analyzed. An advantage of this is that plasma extraction and plasma analysis can be carried out in a fully automated manner.

The system shown in FIG. 11 differs from the system shown in FIG. 10 in that, instead of pneumatic actuation, use is made of mechanical actuation. To this end, the first microchamber 10a in the first substrate 2 can be designed such that the main surface of the first substrate 2 facing away from the second substrate 5 is thinned in the region of the first microchamber 10a. By means of a in the region of the thinned surface of the first substrate 2, a tappet 27 can be used to exert a defined force on the surface of the first substrate 2 such that the thinned surface arches into the first microchamber 10a and produces the overpressure. An advantage of this design is that no pneumatic connectors are required, as a result of which it is possible to avoid having to establish a seal.

The system shown in FIG. 12 differs from the system shown in FIG. 11 in that, instead of a thinning of the surface of the first substrate 2, the first microchamber 10a has a breakthrough through the first substrate 2 and the first substrate 2 is sealed by a blister film 28 in the region of the breakthrough. The tappet 27 can then elastically deform the blister film 28 for the purpose of producing an overpressure in the first microchamber 10a. Advantages of this are that less force is required for the actuation, the first microchamber 10a can have smaller dimensions and the accuracy in terms of manufacturing need not be so precise during the production of the first microchamber 10a.

In the systems explained with reference to FIGS. 5 to 8 and 10 to 12, provision can be made in each case for the first and second substrates 2 and 5 and also optionally the third substrate 19, the first and second thermoplastic connection layers 3 and 6 and also the filter layer 4 to be connected by means of a joining process explained with reference to FIGS. 1 and 2.

It is understood that developments, modifications and specific features and functions of the embodiments explained in conjunction with the respective systems 1, 1a, 1b, 1c, 1d, 1e, 1f, 1g, 1h and 1j can just as well be transferred to the respective systems of the other embodiments.

What is claimed is:

1. A system for separating bodily fluid constituents, comprising:
    a first substrate which, in a first main surface, has a first cavity configured to hold a bodily fluid sample;
    a second substrate which, in a first main surface facing the first substrate, has a second cavity configured to hold constituents separated from the bodily fluid sample, wherein the second cavity lies opposite to the first cavity;
    a filter layer which is arranged between the first substrate and the second substrate and which is configured to separate constituents of the bodily fluid sample in the first cavity and to pass the separated constituents to the second cavity; and
    a first thermoplastic connection layer which is interposed between the first substrate and the filter layer, the first thermoplastic connection layer being connected to both the first main surface and the filter layer,
    wherein the first thermoplastic connection layer is configured to interconnect the first main surface of the first substrate and the filter layer in a fluid-tight manner,
    wherein the first thermoplastic connection layer has a cutout lying opposite to the first cavity,
    wherein the first substrate comprises a first microchannel which is connected to the first cavity and which is configured to be actuated with overpressure such that the bodily fluid sample situated in the first cavity is pressed out of the first cavity through the filter layer,
    wherein the second substrate comprises a first pressure channel on the first main surface, which pressure channel adjoins a main surface of the thermoplastic connection layer,
    wherein the first microchannel adjoins the opposing main surface of the first thermoplastic connection layer, and
    wherein the first pressure channel is configured to be actuated with overpressure such that the first thermoplastic connection layer penetrates into the first microchannel under elastic deformation and produces a corresponding overpressure in the first microchannel.

2. The system according to claim 1, wherein:
    the first cavity extends from the first main surface of the first substrate to a second main surface of the first substrate lying opposite the first main surface, and
    the system furthermore comprises a first adhesive film which is detachably arranged on the second main surface of the first substrate and covers the first cavity.

3. The system according to claim 1, wherein:
    the first cavity extends from the first main surface of the first substrate to a second main surface of the first substrate lying opposite the first main surface, and
    the system furthermore comprises:
        a third substrate which is arranged on the second main surface of the first substrate and covers the first cavity; and
        a second thermoplastic connection layer which is arranged between the third substrate and the first substrate and is configured to interconnect the third substrate and the first substrate in a fluid-tight manner.

4. The system according to claim 1, wherein:
the second substrate has a cutout in the first main surface in which cutout the filter layer is arranged, and
the thermoplastic connection layer is configured to interconnect the first main surface of the first substrate and the first main surface of the second substrate in a fluid-tight manner.

5. The system according to claim 1, wherein:
the second substrate comprises (i) a first microchannel which is connected to the second cavity, and (ii) a second microchannel which is connected to the second cavity, and
the first microchannel is configured to be actuated with overpressure such that the separated constituents of the bodily fluid sample situated in the second cavity are pressed out of the second cavity through the second microchannel.

6. The system according to claim 5, further comprising a microsensor which is arranged in a sensor region in the first main surface of the first substrate or of the second substrate, wherein:
the first thermoplastic connection layer has a cutout lying opposite to the sensor region, and
the second microchannel runs on the first main surface of the second substrate in the region of the cutout lying opposite to the sensor region such that separated constituents of the bodily fluid sample which are pressed through the second microchannel come into contact with the microsensor.

7. The system according to claim 1, wherein the first substrate and the second substrate respectively comprise a transparent thermoplastic material.

8. The system according to claim 1, wherein the first thermoplastic connection layer is fused to the filter layer,
wherein a stable and fluid-tight connection between the filter layer and the first thermoplastic connection layer is created by capillary penetration of the fused first thermoplastic connection layer into the filter layer.

9. The system according to claim 1, wherein the filter layer comprises a fabric filter, a silica filter, or plasma separation membrane.

10. The system according to claim 5, wherein dimensions of the second cavity and the first and the second microchannels are selected to set an amount of volume displaced.

11. The system according to claim 1, wherein mechanical actuation is used to produce the overpressure in the first cavity.

12. The system according to claim 11, wherein the mechanical actuation comprises a tappet.

13. The system according to claim 12, wherein a blister film is elastically deformable by the tappet to produce the overpressure in the first cavity.

* * * * *